United States Patent
Cai et al.

(10) Patent No.: US 12,208,233 B2
(45) Date of Patent: Jan. 28, 2025

(54) DRIP CHAMBER INSERT FOR AUTOMATICALLY REDUCING FLUID FLOW RATE AT INFUSION COMPLETION TO KEEP VEIN OPEN

(71) Applicant: CareFusion 303, Inc., San Diego, CA (US)

(72) Inventors: Frank Cai, Ontario, CA (US); Jason Andrew Wine, Placentia, CA (US)

(73) Assignee: CareFusion 303, Inc., San Diego, CA (US)

( * ) Notice: Subject to any disclaimer, the term of this patent is extended or adjusted under 35 U.S.C. 154(b) by 906 days.

(21) Appl. No.: 17/341,070

(22) Filed: Jun. 7, 2021

(65) Prior Publication Data

US 2022/0387707 A1    Dec. 8, 2022

(51) Int. Cl.
  *A61M 5/14* (2006.01)
  *A61M 5/165* (2006.01)
  *A61M 5/168* (2006.01)

(52) U.S. Cl.
  CPC .......... *A61M 5/1411* (2013.01); *A61M 5/165* (2013.01); *A61M 5/16813* (2013.01); *A61M 2005/1404* (2013.01); *A61M 2005/1657* (2013.01); *A61M 2205/75* (2013.01); *A61M 2205/7527* (2013.01)

(58) Field of Classification Search
  CPC .. A61M 2005/1401; A61M 2005/1404; A61M 2005/1652; A61M 2005/1657; A61M 2205/75; A61M 2205/7527; A61M 5/14; A61M 5/1411; A61M 5/165; A61M 5/168; A61M 5/16804; A61M 5/16813; A61M 5/16877; A61M 5/16886; A61M 5/1689; A61M 5/36; A61M 5/38
  See application file for complete search history.

(56) References Cited

U.S. PATENT DOCUMENTS 4,173,222 A    11/1979  Muetterties
5,188,603 A     2/1993  Vaillancourt

FOREIGN PATENT DOCUMENTS

WO    WO-2005079886 A3    9/2005
WO    WO-2020254814 A1   12/2020

OTHER PUBLICATIONS

International Search Report and Written Opinion for Application No. PCT/US2022/029921, dated Sep. 16, 2022, 14 pages.

*Primary Examiner* — Shefali D Patel
(74) *Attorney, Agent, or Firm* — Morgan, Lewis & Bockius LLP

(57) ABSTRACT

A drip chamber insert may include an elongate body portion comprising an upper surface, and a base portion positioned downstream of the elongate body portion for coupling to a drip chamber. The base portion may have an upper surface and a lower surface defining an outlet orifice of the drip chamber insert. The drip chamber insert may further include a first chamber and a second chamber. The first chamber may be disposed in the elongate body portion and fluidly coupled to the upper surface of the elongate body portion via an inlet orifice and to the outlet orifice via the base portion. An anti-run-dry membrane may be disposed on the upper surface of the elongate body portion extending over the inlet orifice. The second chamber may be disposed in the elongate body portion extending from the upper surface of the elongate body portion to the base portion. A low flowrate orifice may extend from a base of the second chamber into the base portion for fluidly coupling the second chamber with the outlet orifice.

20 Claims, 5 Drawing Sheets

DRIP CHAMBER INSERT FOR AUTOMATICALLY REDUCING FLUID FLOW RATE AT INFUSION COMPLETION TO KEEP VEIN OPEN

TECHNICAL FIELD

The present disclosure generally relates to drip chambers, and in particular to a drip chamber including an insert capable of slowing down the flow rate of the final volume of fluid in the drip chamber towards completion of infusion to allow the patient's vein to stay open.

BACKGROUND

The present invention is generally directed to systems and methods for intravenous ("IV") delivery, by which fluids can be administered directly to a patient. An intravenous delivery system according to the present disclosure is used broadly herein to describe components used to deliver the fluid to the patient, for use in arterial, intravenous, intravascular, peritoneal, and/or non-vascular administration of fluid. Of course, one of skill in the art may use an intravenous delivery system to administer fluids to other locations within a patient's body.

One common method of administering fluids into a patient's blood flow is through an intravenous delivery system. In many common implementations, an intravenous delivery system may include a liquid source such as a liquid bag, a drip chamber used to determine the flow rate of fluid from the liquid bag, tubing for providing a connection between the liquid bag and the patient, and an intravenous access unit, such as a catheter that may be positioned intravenously in a patient. An intravenous delivery system may also include a Y-connector that allows for the piggybacking of intravenous delivery systems and for the administration of medicine from a syringe into the tubing of the intravenous delivery system.

During infusion with gravity sets or pumps, an unattended complete infusion can lead to a loss of patency in the catheter due to blood diffusing back through the catheter tip. The blood will begin to coagulate, which may seal off the flow in the catheter, making it unusable.

The description provided in the background section should not be assumed to be prior art merely because it is mentioned in or associated with the background section. The background section may include information that describes one or more aspects of the subject technology.

SUMMARY

In accordance with various embodiments of the present disclosure, a drip chamber insert may include an elongate body portion having an upper surface, and a base portion positioned downstream of the elongate body portion for coupling to a drip chamber. The base portion may have an upper surface and a lower surface defining an outlet orifice of the drip chamber insert. The drip chamber insert may further include a first chamber disposed in the elongate body portion and fluidly coupled to the upper surface via an inlet orifice and to the outlet orifice via the base portion, an anti-run-dry membrane disposed on the upper surface of the elongate body portion extending over the inlet orifice, and a second chamber disposed in the longitudinally extending body and extending from the upper surface to the base portion. A low flowrate orifice may extend from a base of the second chamber into the base portion for fluidly coupling the second chamber with the outlet orifice.

In accordance with various embodiments of the present disclosure, a drip chamber assembly may include a drip chamber including a housing having an inlet for receiving an IV fluid, an outlet for dispensing the IV fluid to a patient, and a cavity defined by an inner surface of the housing. A drip chamber insert may be disposed in the cavity. The drip chamber insert may include an elongate body portion having an upper surface, and a base portion positioned downstream of the elongate body portion, the base portion. The base portion may define an outlet orifice of the drip chamber insert and may be fluidly connected to the outlet of the drip chamber. The drip chamber may further include a first chamber disposed in the elongate body portion, a second chamber disposed in the elongate body portion and extending from the upper surface to the base portion, and a low flowrate orifice extending from a base of the second chamber into the base portion for fluidly coupling the second chamber with the drip chamber outlet. The first chamber may include an inlet orifice fluidly coupling the first chamber to the upper surface of the elongate body portion, and an anti-run-dry membrane disposed on the upper surface of the elongate body portion extending over the inlet orifice. The inlet orifice may be fluidly coupled to the drip chamber inlet for receiving the IV fluid in a first flow condition. The second chamber may have an open proximal end for receiving at least a portion of the IV fluid in a second flow condition.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

The following figures are included to illustrate certain aspects of the embodiments and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figure 1:
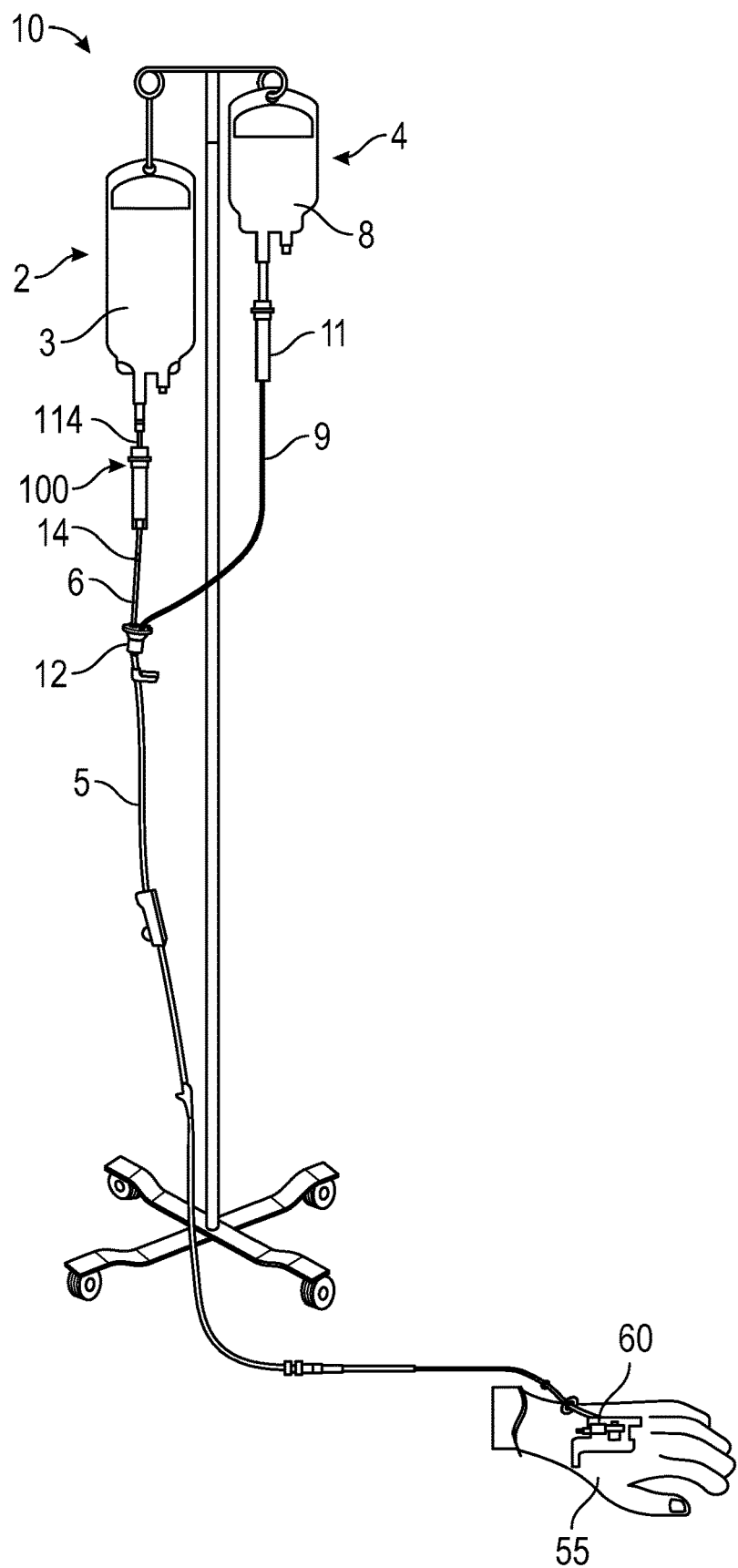
FIG. 1 illustrates an IV extension set that includes a drip chamber assembly, in accordance with some embodiments of the present disclosure.

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular, but non-limiting, examples. Various embodiments described in the present disclosure may be carried out in different ways and variations, and in accordance with a desired application or implementation.

During infusion with gravity sets or a pump that does not have a keep-vein-open (KVO) function, an unattended complete infusion can lead to a loss of patency in the catheter due to blood diffusing back through the catheter tip. The blood will begin to coagulate, which will seal off the flow in the catheter, making it unusable. If infusion is to continue, the clinician must remove the catheter and re-insert a new one into the patient, which is costly, painful to the patient, and time consuming.

Some gravity sets attempt to address the above issue by employing a device that utilizes the patient's blood pressure to flow out through an injection site into a container with a plunger. The device is used mainly for keeping the vein open during the infusion of contrast media. The plunger is driven back with the blood pressure and can be driven with a motor to help draw out blood if the blood pressure is not enough to drive the plunger.

The present description relates in general to drip chambers, and in particular to a drip chamber including a drip chamber insert capable of slowing down the flow rate of the final volume of fluid in the drip chamber towards completion of infusion to allow the patient's vein to stay open until a clinician can tend to the completed infusion.

According to various embodiments of the present disclosure, the drip chamber assembly may be fluidly coupled to a catheter which may be inserted into a vein of a patient for infusion of an IV fluid and/or blood draw. In some embodiments, the drip chamber assembly may include a drip chamber having an additional component mounted or otherwise affixed therein. The additional component may be welded, glued, or otherwise similarly affixed to a base portion of the drip chamber. In some embodiments, the additional component may be a drip chamber insert that is affixed (for example, but not limited to welded or glued) into the drip chamber with the capability of slowing down the flow of the final volume (for example, but not limited to the final 10-60 milliliters (ml)) of IV fluid remaining in the drip chamber after depletion of the IV fluid in the IV fluid bag. The slowing of the flow rate of the IV fluid at completion of the infusion may advantageously allow a patient's vein to stay open longer until a clinician can tend to the completed infusion.

In some embodiments, the drip chamber insert may split or otherwise partition the drip chamber into two chambers: (i) a first chamber having an inlet orifice (also referred to herein as a normal flow orifice) for normal, unrestricted flow of the IV fluid, and (ii) a second chamber with a small orifice at a bottom or base of the second chamber that allows for a greatly reduced keep-vein-open (KVO) flow rate of the IV fluid. In some embodiments, an anti-run-dry filter or membrane may be attached to an upper surface of drip chamber insert extending over the top of the normal flow orifice to ensure that when the IV fluid in the drip chamber falls below the predetermined threshold value, the anti-run-dry membrane may restrict or otherwise block the remaining IV fluid from entering the normal fluid pathway in the first chamber. Accordingly, the remaining IV fluid in the drip chamber will flow through the path of less fluid flow resistance; the KVO fluid pathway delivers fluid to the patient at the greatly reduced flowrate via the low flowrate orifice.

For example, in some embodiments, the normal fluid pathway may deliver the fluid at a flow rate ranging from about 50 milliliters/hour (ml/hr) to about 1000 ml/hr, in some instances ranging from about 200 ml/hr to 800 ml/hr, more typically from about 400 ml/hr to 600 ml/hr, and in some embodiments approximately 500 ml/hr. In contrast, in some embodiments, the KVO fluid pathway may deliver the fluid at a reduced flow rate ranging from about 2 ml/hr to about 10 ml/hr, in some instances ranging from about 3 ml/hr to 9 ml/hr, more typically from about 5 ml/hr to 7 ml/hr, and in some embodiments approximately 6 ml/hr. Accordingly, towards completion of infusion, the IV fluid may be dispensed to the patient via the low flowrate orifice to allow the patient's vein to stay open until a clinician can tend to the completed infusion.

Though recited in terms of certain ranges, it will be understood that all ranges from the lowest of the lower limits to the highest of the upper limits are included, including all intermediate ranges or specific angles, within this full range or any specifically recited range.

According to various embodiments of the present disclosure, the IV set including the drip chamber and drip chamber insert may mainly rely on gravity or suction from a pump for flow of the IV fluid. Once flow above the drip chamber stops (e.g., upon depletion of the IV fluid in the IV bag), the IV fluid in the drip chamber will continue to flow into the IV tubing to the patient. When the IV fluid level in the drip chamber drops to a predetermined threshold level, for example, a level corresponding to the height of the anti-run-dry membrane, the normal fluid path is blocked by the anti-run-dry membrane, thereby causing the remaining IV fluid to proceed through the KVO path and to the patient via the low flowrate orifice. The small orifice significantly lowers the flow rate of the remainder of the IV fluid.

Accordingly, the various embodiments of the present disclosure are advantageous in providing a drip chamber assembly capable of dispensing the last few milliliters of IV fluid to a patient at a reduced flow rate in order to keep the vein open once the IV fluid in the IV bag is depleted. The drip chamber assembly with drip chamber insert of the various embodiments described herein is further advantageous as it does not require modifications to the existing drip chamber other than affixing the drip chamber insert therein, thus only minimal change to the currently existing IV sets is necessary. As can be appreciated, no modifications to the pump are required. Further advantageously, the drip chamber insert does not require complex electronics or other technology in order to be integrated into the currently existing drip chamber. The drip chamber insert accomplishes the described function as a mechanical device with a mechanical connection. Additionally, the drip chamber assembly with the drip chamber insert of the various embodiments described herein is advantageous in that no additional training is required to use it. Further advantages are realized in time savings with respect to infusion therapy time for the medical personnel by eliminating the need to reinsert the catheter due to blood coagulation, which is commonly associated with gravity sets or pumps that do not have a keep-vein-open (KVO) function. Furthermore, since the catheter does not need to be reinserted, this has the effect of reducing or otherwise eliminating pain to the patient associated with reinserting the catheter.

FIG. 1 illustrates a multiple line IV extension set 10 that includes a drip chamber assembly 100 in accordance with some embodiments of the present disclosure. The drip chamber assembly 100 may be fluidly coupled to a catheter 60 which may be inserted into a vein of a patient for infusion of an IV fluid and/or blood draw. As depicted, IV set 10 includes a primary fluid system 2 and a secondary fluid system 4. An IV pump (not shown) receives fluid from primary fluid system 2 and secondary fluid system 4 via a primary IV fluid line 5 and a secondary IV fluid line 7, and may control and dispense the fluids therefrom to a patient 55.

In some embodiments, primary fluid system 2 may include a primary fluid source or container such as a primary intravenous (IV) fluid bag 3, which may include or contain a first medical fluid, for example, saline solution or other medicinal fluid or drug to be administered to the patient. As illustrated, IV tubing 116 may carry flow from the drip chamber assembly 100 to a Y-connector 12. Check valve 14 may be disposed in tube 6 upstream from the Y-connector 12 and enables flow from fluid bag 3 to the IV pump (not illustrated) while preventing reverse flow (backflow) of fluid from auxiliary fluid system 4 toward fluid bag 3.

In accordance with some embodiments, secondary fluid system 4 may include a secondary fluid source or container such as a secondary IV fluid bag 8, which may contain a second medical fluid, for example, drugs or other secondary fluid to be supplied to the patient 55 for treatment via the catheter 60. A secondary fluid line 9 carries flow from a drip chamber 11 to the Y-connector 12.

In some embodiments, the second medical fluid may be different from the first medical fluid. However, the various embodiments of the present disclosure are not limited to the aforementioned configuration. In other embodiments, the first and second fluids may be the same.

According to various embodiments of the present disclosure, as illustrated in FIG. 1, primary IV fluid bag 3, which holds a primary fluid, may be positioned at a lower axial position or height than the secondary IV fluid bag 8. For example, the primary IV fluid bag 3 may be hung on a suspension system or hanger and then the secondary IV fluid bag 8 may be hung above the primary IV fluid bag 10 and may be coupled to the secondary fluid line 9, which may be connected to the primary fluid line 5 via a connector (e.g., a y-site connector).

Figure 2:
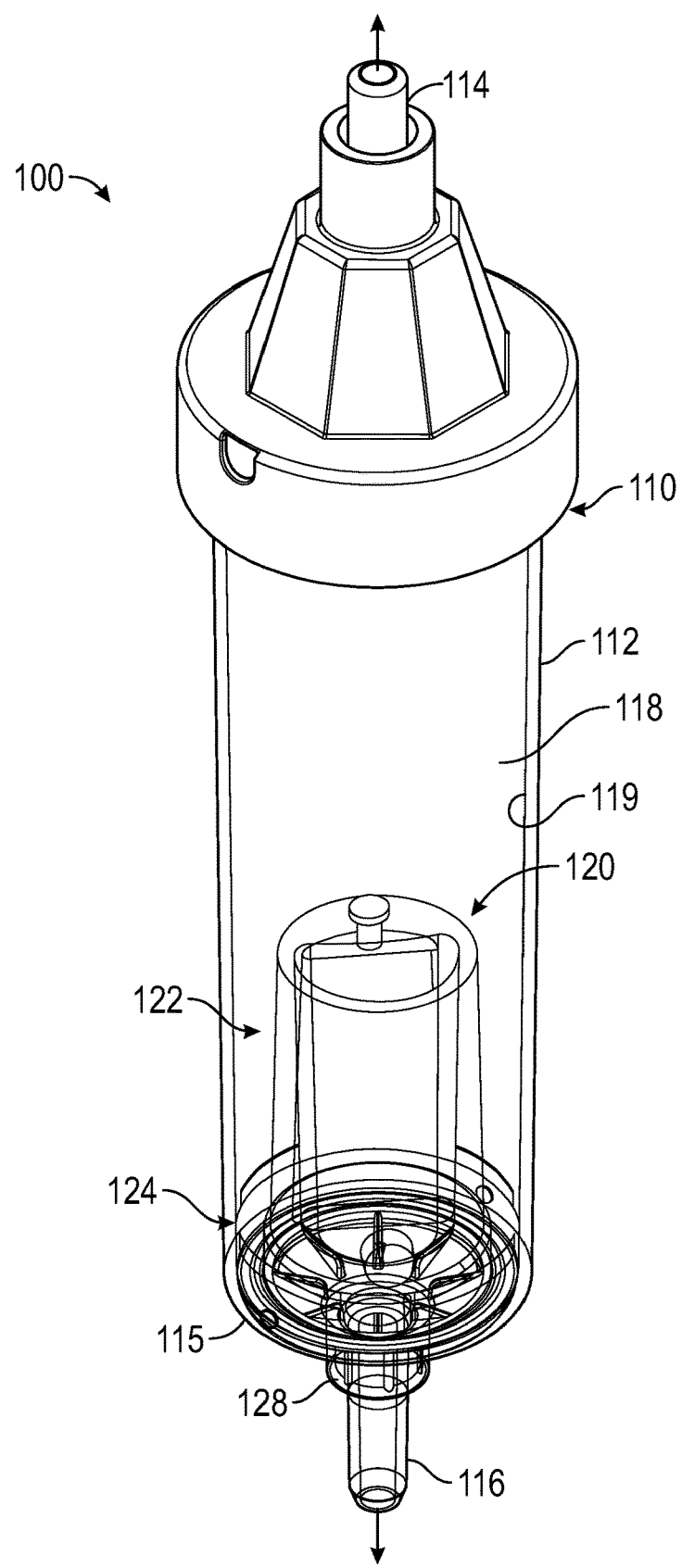
FIG. 2 illustrates a perspective view of the drip chamber assembly, in accordance with some embodiments of the present disclosure.

FIG. 2 illustrates a perspective view of the drip chamber assembly 100, in accordance with some embodiments of the present disclosure. According to various embodiments of the present disclosure, a drip chamber assembly 100 may include a drip chamber 110 and a drip chamber insert 120. The drip chamber 110 may include a housing 112 having an inlet 114 for receiving an IV fluid, an outlet 116 for dispensing the IV fluid to a patient, and a cavity 118 defined by an inner surface 119 of the housing 112. As depicted, the drip chamber insert 120 may be disposed in the cavity 118 of the drip chamber housing 112.

Figure 3:
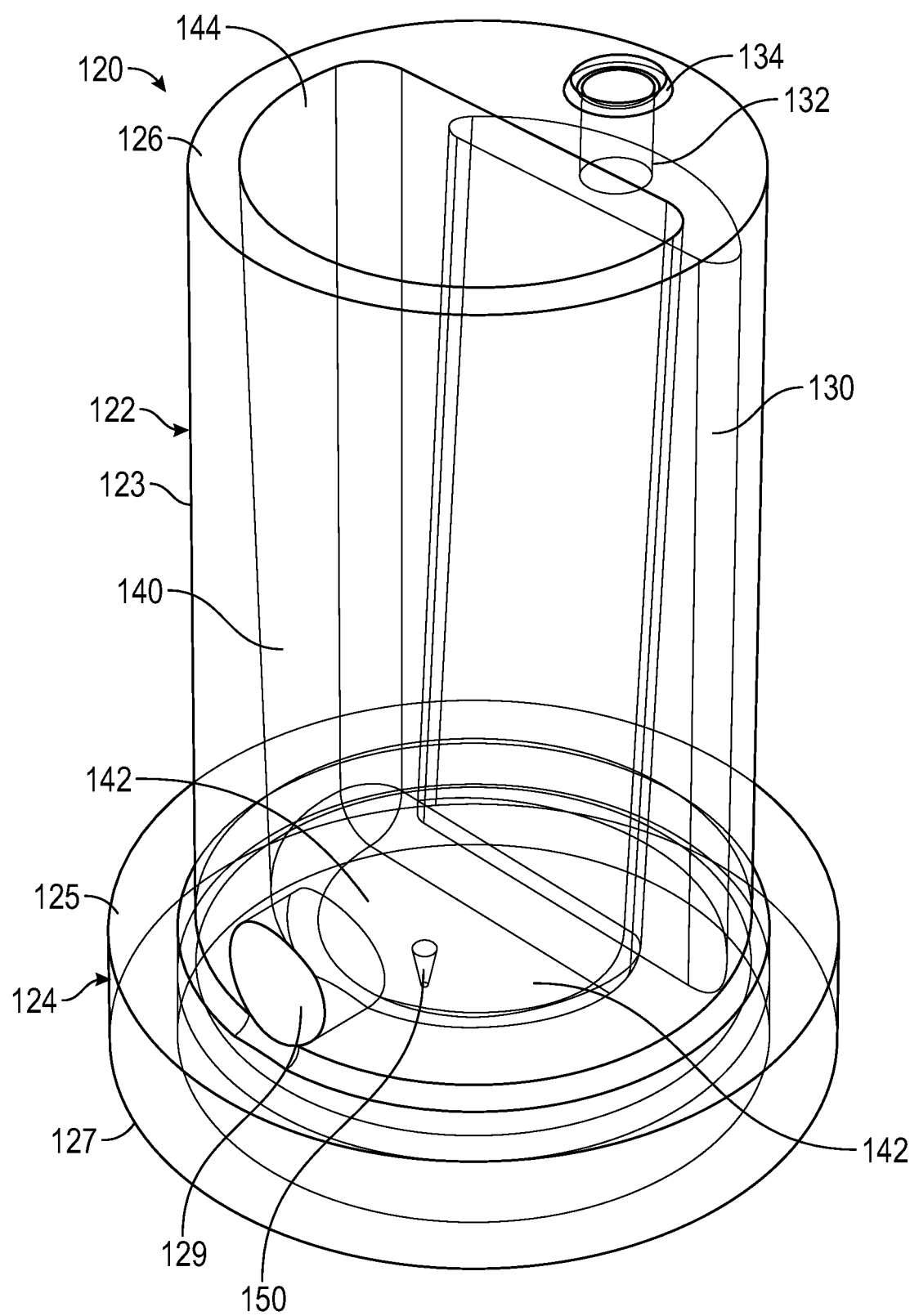
FIG. 3 illustrates a perspective view of a drip chamber and drip chamber insert of the drip chamber assembly of FIG. 2, in accordance with some embodiments of the present disclosure.

FIG. 3 illustrates a perspective view of the drip chamber 110 and drip chamber insert 120 of the drip chamber assembly 100 of FIG. 2, in accordance with some embodiments of the present disclosure. In some embodiments, the drip chamber insert 120 may include a longitudinally extending or elongate body portion 122 having an upper surface 126 and a base portion 124 disposed downstream or at a distal end of the elongate body portion 122. The base portion 124 may define an outlet orifice 128 of the drip chamber insert 120 and be fluidly connected to the outlet 116 of the drip chamber 110. In some embodiments, the drip chamber insert 120 may include a first chamber 130 and a second chamber 140 disposed in the elongate body portion 122. The first chamber may include an inlet orifice 132 for receiving an IV fluid. An anti-run-dry membrane 134 may be disposed on the upper surface 126 of the elongate body portion 122 extending over the inlet orifice 132. In some embodiments, the anti-run-dry membrane 134 may be positioned at the inlet such that the IV fluid 50, flowing from the IV fluid source (e.g., IV bag 10), passes through the anti-run-dry membrane 134. The anti-run-dry membrane 134 may have a plurality of pores, through which the IV fluid 50 flows, and may be formed of a hydrophilic material that resists passage of air through the pores while allowing liquid to pass through the pores.

Figure 4:
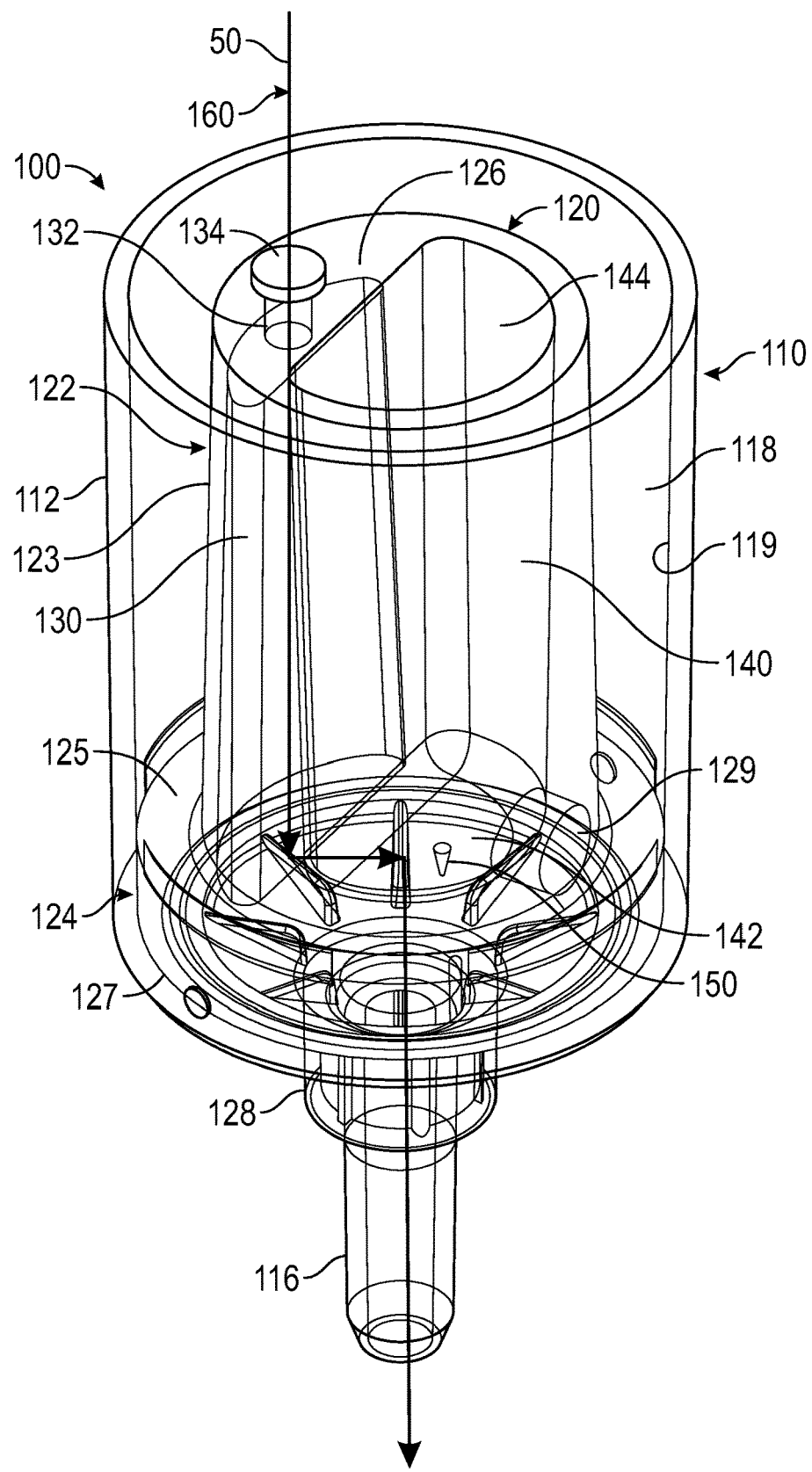
FIG. 4 illustrates a perspective view of the drip chamber and drip chamber insert of FIG. 3 in a first flow condition, in accordance with some embodiments of the present disclosure.

In some embodiments, the inlet orifice 132 may be fluidly coupled to the drip chamber inlet 114 for receiving the IV fluid 50 in a first flow condition (illustrated in FIG. 4). The first flow condition as defined herein refers to a condition or state in which IV fluid flows in a regular or normal manner from the IV tubing into the drip chamber insert 120 and out through the drip chamber outlet 116 without otherwise being blocked, slowed down, reduced, or impeded by the drip chamber insert 120.

As depicted, the second chamber 140 may be disposed in the elongate body portion 122 and extend from the upper surface 126 to the base portion 124. The second chamber 140 may have an open proximal end 144 for receiving at least a portion of the IV fluid 50 in a second flow condition (illustrated in FIG. 5). The second flow condition as defined herein refers to a keep-vein-open condition or state in which the flow rate of the final milliliters (ml) (for example, but not limited to the last 10-60 ml) of IV fluid in the drip chamber 110 exiting the drip chamber assembly 100 via the drip chamber assembly outlet orifice 128 is slowed down, reduced, or impeded so as to keep a vein of the patient open upon depletion of the IV fluid in the IV fluid bag 10. To this effect, in some embodiments, the drip chamber insert 120 may further include a low flowrate orifice 150 extending from a distal end 142 of the second chamber 140 into the base portion 124 for fluidly coupling the second chamber 140 with the drip chamber outlet 116. In some embodiments, the low flowrate orifice 150 may have a shape configured to slow down or otherwise reduce the rate at which the IV fluid passes from the drip chamber assembly into the drip chamber assembly outlet orifice 128. For example, in some embodiments, the low flowrate orifice 150 may have a conical shape which tapers or otherwise reduces in diameter or cross-section distally into the base portion 124, towards the outlet 116.

For example, in some embodiments, the normal fluid pathway may deliver the fluid at a flow rate ranging from about 50 milliliters/hour (ml/hr) to about 1000 ml/hr, in some instances ranging from about 200 ml/hr to 800 ml/hr, more typically from about 400 ml/hr to 600 ml/hr, and in some embodiments approximately 500 ml/hr. In contrast, in some embodiments, the KVO fluid pathway may deliver the fluid at the reduced or slowed-down flow rate ranging from about 2 ml/hr to about 10 ml/hr, in some instances ranging from about 3 ml/hr to 9 ml/hr, more typically from about 5 ml/hr to 7 ml/hr, and in some embodiments approximately 6 ml/hr. As a further example, in some embodiments, the KVO fluid pathway may deliver the fluid at a slower or reduced rate in the range of about 1% to 15% of the flow rate through the normal fluid pathway, in some instances in the range of about 2% to 10% of the flow rate through the normal fluid pathway, more typically from about 3% to 5% of the flow rate through the normal fluid pathway, and in some embodiments approximately 4% of the flow rate through the normal fluid pathway. Though recited in terms of certain ranges, it will be understood that all ranges from the lowest of the lower limits to the highest of the upper limits are included, including all intermediate ranges or specific angles, within this full range or any specifically recited range.

According to various embodiments of the present disclosure, the elongate body portion 122 may further include a sidewall 123 longitudinally extending between the upper surface 126 and the base portion 124. In particular, the sidewall 123 may extend from the upper surface 126 to a proximal end 125 of the base portion 124. As depicted, the elongate body portion 122 may further include a fluid bypass orifice 129 disposed in the sidewall 123. The fluid bypass orifice 129 may be fluidly coupled to the drip chamber outlet 116 via the low flowrate orifice 150 and the drip chamber insert outlet orifice 128.

FIG. 4 illustrates a perspective view of the drip chamber 110 and drip chamber insert 120 of FIG. 3 in the first flow condition, in accordance with some embodiments of the present disclosure. As depicted, the inlet orifice 132, the first chamber 130, the drip chamber insert outlet orifice 128 and the drip chamber outlet 116 may be fluidly coupled to define a first fluid pathway 160. In operation, IV fluid 50 flows from the fluid source (e.g., the primary intravenous (IV) fluid bag 10) into the drip chamber 110. So long as the fluid in the drip chamber 110 remains above a predetermined fluid level, the first flow condition is activated and the IV fluid 50 exits the drip chamber assembly 100 via the first fluid pathway 160. In some embodiments, the predetermined fluid level may be greater than or equal to 60 ml. However, the various embodiments of the present disclosure are not limited to this configuration. For example, in some embodiments, the predetermined fluid level may range from about 10-60 ml, in some instances range from about 20-50 ml, in other instances from about 30-40 ml, and in some embodiments approximately 35 ml. In some embodiments, a volume of the drip chamber insert 120 may range from about 2-10 ml. In yet other embodiments, where a burette may be used in place of the drip chamber insert, a volume capacity of the burette may be as high as up to 150 ml. Though recited in terms of certain ranges, it will be understood that all ranges from the lowest of the lower limits to the highest of the upper limits are included, including all intermediate ranges or specific angles, within this full range or any specifically recited range.

In accordance with various embodiments of the present disclosure, in the first flow condition where IV fluid in the drip chamber 110 is above a predetermined level, the IV fluid flowing from the IV bag 10 into the drip chamber assembly 100 passes through the anti-run-dry membrane 134 and enters the first chamber 130 via the inlet orifice 132. In some embodiments, the predetermined level may be defined as the height at which the anti-run-dry membrane 134 is positioned. As depicted in FIG. 4, in the first flow condition, the IV fluid flows in the first fluid pathway 160 in a uniform continuous unrestricted/unconstrained manner through the first chamber 130 and into the IV tubing 116 via the drip chamber insert outlet orifice 128 and out of the drip chamber outlet 116. Accordingly, the IV fluid may be timely and continuously infused to a patient for example in the first flow condition (e.g., a standard infusion operation). In operation, as the infusion of the IV fluid continues, the IV fluid in the IV bag 10 may be depleted thereby causing a corresponding decrease of the level of IV fluid in the drip chamber 110 as the fluid continues to be dispensed into the IV tubing 116. When the level of the IV fluid in the drip chamber 110 falls below the predetermined level, for example, but not limited to between 10 ml to 60 ml, the anti-run-dry membrane 134 as positioned over the inlet orifice 132 may enable a fluid column of significant length to be maintained within the first chamber 130 and the IV tubing 116 after cessation of flow of the IV fluid 50 from the IV bag 10 into drip chamber 110, without permitting further IV fluid 50 to flow into the first chamber 130.

In particular, in operation, once the IV fluid 50 stops flowing into the drip chamber 110, for example, due to depletion of the IV fluid 50 in the IV fluid bag 10, and the level of IV fluid in the drip chamber 110 falls below the predetermined level (e.g., the height at which the anti-run-dry membrane 134 is positioned), the anti-run-dry membrane 134 may act to restrict motion of IV fluid 50 into the inlet orifice 132. For example, the anti-run-dry membrane 134 may have a plurality of pores, each of which has a size that causes the formation of a meniscus of the IV fluid 50 underneath the anti-run-dry membrane 134. Each meniscus may, via capillary action, contribute to the support of a column of the IV fluid 50 in the first chamber 130 and IV tubing 116. The anti-run-dry membrane 134 may thus be designed to facilitate support of the column of the IV fluid 50 within the first chamber 130. In some embodiments, the anti-run-dry membrane may become saturated by means of the capillary action. In this condition, the pores of the anti-run-dry membrane 134 may become filled with fluid thereby providing increased resistance to flow of the IV fluid remaining in the drip chamber 110 into the first fluid pathway 160. Accordingly, in this second flow condition the anti-run-dry membrane 134 may serve to block the first fluid pathway 160 to the IV fluid remaining in the drip chamber 110.

Figure 5:
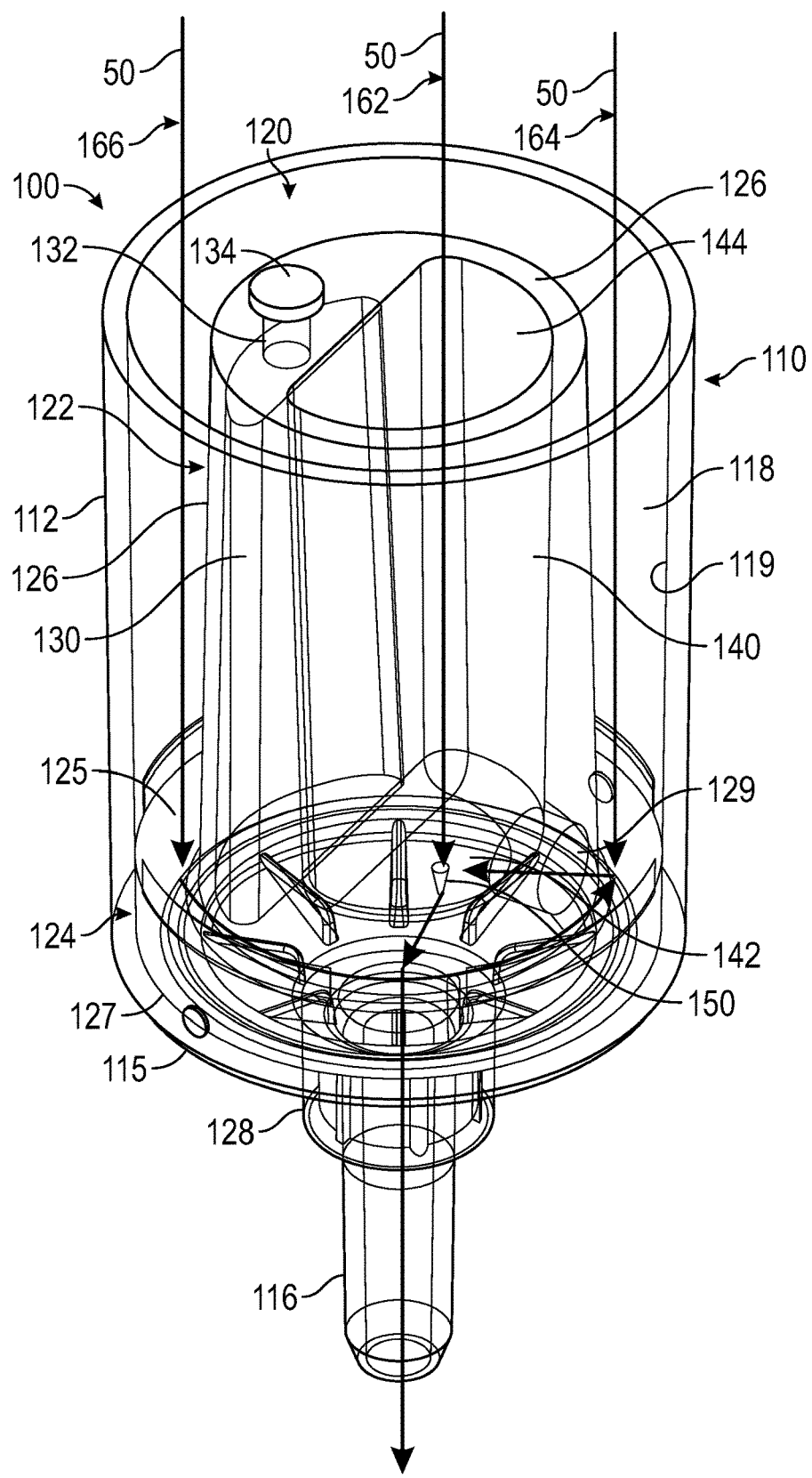
FIG. 5 illustrates a perspective view of the drip chamber and drip chamber insert of FIG. 3 in a second flow condition, in accordance with some embodiments of the present disclosure.

FIG. 5 illustrates a perspective view of the drip chamber 110 and drip chamber insert 120 of FIG. 3 in the second flow condition, in accordance with some embodiments of the present disclosure. As depicted, the open proximal end 144 of the second chamber 140, the low flowrate orifice 150, the drip chamber insert outlet orifice 128, and the drip chamber outlet 116 may be fluidly coupled to define a second fluid pathway 162. As further depicted, a third fluid pathway 164 may be defined longitudinally between the sidewall 123 of the elongate body portion 122 and the inner surface 119 of the drip chamber 110, through the fluid bypass orifice 150, and into the drip chamber insert outlet orifice 128 and the drip chamber outlet 116 via the low flowrate orifice 150. In some embodiments, a fourth fluid pathway 166 may be defined longitudinally between the sidewall 123 of the elongate body portion 122 and the inner surface 119 of the drip chamber 110, and circumferentially along an upper surface 125 of the base portion 122 between the sidewall 123 of the elongate body portion 122 and the inner surface 119 of the drip chamber 110, through the fluid bypass orifice 129, and into the outlet orifice 128 via the low flowrate orifice.

According to various embodiments of the present disclosure, the second, third, and fourth fluid pathways 162, 164 and 166 may collectively define a keep-vein-open fluid path in the second flow condition. In particular, as described above, when the IV fluid in the drip chamber falls below the predetermined level (e.g., the height at which the anti-run-dry membrane 134 is positioned) the anti-run-dry membrane 134 may prevent the remaining IV fluid from flowing into the drip chamber assembly outlet orifice 128 via the inlet orifice such that the remaining IV fluid flows through the second, third, and fourth fluid pathways 162, 164 and 166 defining the keep-vein-open fluid path having less resistance to flow than the obstructed first fluid pathway.

The aforementioned configuration of the drip chamber assembly having the drip chamber insert as described above is advantageous in that drip chamber insert 120 may be fixed (for example, welded or glued) into the drip chamber 110 functions to slow down the final milliliters (for example, but not limited to, the last 10-60 ml) of IV fluid in the drip chamber 110. This slowing towards the end of the infusion allows the patient's vein to stay open longer until a clinician can tend to the finished infusion. The drip chamber insert 120 may split the drip chamber into two chambers; the first chamber for normal flow, and the second chamber with the low flowrate orifice at the bottom that allows for a greatly reduced flow rate as compared to the flowrate through the first chamber in the first flow condition (i.e., standard infusion flow). The anti-run-dry filter 134 attached to the top of the inlet orifice 132 (also referred to herein as the normal flow orifice) ensures that when the IV fluid in the drip chamber is low enough, the first fluid pathway 160 is stopped and the KVO fluid pathway 162, 164, and 166 has less resistance to fluid flow, thereby allowing the IV fluid to be administered to the patient via the outlet 116 at low flow rates sufficient to just keep the vein open.

Accordingly, the various embodiments of the present disclosure are advantageous in providing a drip chamber assembly capable of dispensing the last few milliliters of IV fluid to a patient at a reduced flow rate in order to keep the vein open once the IV fluid in the IV bag is depleted. The drip chamber assembly with drip chamber insert of the various embodiments described herein is further advantageous as it does not require modifications to the existing drip chamber other than affixing the drip chamber insert therein, thus only minimal change to the currently existing IV sets is made. As can be appreciated, no modifications to the pump are required. Further advantageously, the drip chamber insert does not require complex electronics or other technology in order to be integrated into the currently existing drip chamber. The drip chamber insert is a mechanical device with mechanical connection. Additionally, the drip chamber assembly with drip chamber insert of the various embodiments described herein is advantageous in that no additional training required to use it. Further advantages are realized in time savings with respect to infusion therapy time for the medical personnel by eliminating the need to reinsert the catheter due to blood coagulation, which is commonly associated with gravity sets or pumps that do not have a keep-vein-open (KVO) function. Furthermore, since the catheter does not need to be reinserted, the drip chamber insert can reduce or otherwise eliminate pain to the patient associated with reinserting the catheter.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, or operations in the processes or methods disclosed are illustrations of exemplary approaches. Based upon implementation preferences or scenarios, it is understood that the specific order or hierarchy of steps, operations or processes may be rearranged. Some of the steps, operations or processes may be performed simultaneously. In some implementation preferences or scenarios, certain operations may or may not be performed. Some or all of the steps, operations, or processes may be performed automatically, without the intervention of a user. The accompanying method claims present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A drip chamber insert, comprising:
    an elongate body portion comprising an upper surface, and a base portion positioned downstream of the elongate body portion for coupling to a drip chamber, the base portion having an upper surface, and a lower surface defining an outlet orifice of the drip chamber insert;
    a first chamber disposed in the elongate body portion and fluidly coupled to the upper surface of the elongate body portion via an inlet orifice and to the outlet orifice via the base portion;
    an anti-run-dry membrane disposed on the upper surface of the elongate body portion extending over the inlet orifice;
    a second chamber disposed in the elongate body portion and extending from the upper surface of the elongate body portion to the base portion; and
    a low flowrate orifice extending from a base of the second chamber into the base portion for fluidly coupling the second chamber with the outlet orifice.

2. The drip chamber insert of claim 1, wherein the elongate body portion further comprises a sidewall longitudinally extending between the upper surface of the elongate body portion and the base portion, and a fluid bypass orifice disposed in the sidewall, the fluid bypass orifice fluidly coupled to the outlet orifice via the low flowrate orifice.

3. The drip chamber insert of claim 2, wherein the low flowrate orifice comprises a conical shape tapering distally into the base portion.

4. The drip chamber insert of claim 2, wherein the inlet orifice, the first chamber and the outlet orifice are fluidly coupled to define a first fluid pathway, and in a first flow condition where fluid in the drip chamber is above a predetermined level, the fluid flowing from a fluid source into the drip chamber passes through the anti-run-dry membrane and enters the first chamber via the inlet orifice and exits the drip chamber insert via the outlet orifice.

5. The drip chamber insert of claim 4, wherein the anti-run-dry membrane is positioned at a predetermined height above the base portion, and the predetermined level of the fluid in the drip chamber is equal to the predetermined height.

6. The drip chamber insert of claim 4, wherein the anti-run-dry membrane comprises a hydrophilic material having a plurality of pores through which the fluid flows.

7. The drip chamber insert of claim 6, wherein an open proximal end of the second chamber, the low flowrate orifice, and the outlet orifice are fluidly coupled to define a second fluid pathway.

8. The drip chamber insert of claim 7, wherein a third fluid pathway is defined longitudinally between the sidewall of the elongate body portion and an inner surface of the drip chamber, through the fluid bypass orifice, and into the outlet orifice via the low flowrate orifice.

9. The drip chamber insert of claim 8, wherein a fourth fluid pathway is defined (i) longitudinally between the sidewall of the elongate body portion and the inner surface of the drip chamber, (ii) circumferentially along the upper surface of the base portion between the sidewall of the elongate body portion and the inner surface of the drip chamber, (iii) through the fluid bypass orifice, and (iv) into the outlet orifice via the low flowrate orifice.

10. The drip chamber insert of claim 9, wherein the second fluid pathway, the third fluid pathway, and the fourth fluid path way restrict a rate at which the fluid leaves the drip chamber insert, and when in a second flow condition, when the fluid in the drip chamber falls below the predetermined level, the anti-run-dry membrane supports a column of the fluid in the first chamber to limit the fluid in the drip chamber from entering the inlet orifice such that the fluid flows through the second fluid pathway, the third fluid pathway, and the fourth fluid pathway.

11. The drip chamber insert of claim 10, wherein the predetermined level that the fluid in the drip chamber falls below in the second flow condition is less than or equal to 60 milliliters.

12. A drip chamber assembly, comprising:
    a drip chamber, including a housing having an inlet for receiving an IV fluid, an outlet for dispensing the IV fluid to a patient, and a cavity defined by an inner surface of the housing; and
    a drip chamber insert disposed in the cavity, the drip chamber insert including:

an elongate body portion comprising an upper surface, and a base portion positioned downstream of the elongate body portion, the base portion defining an outlet orifice of the drip chamber insert and fluidly connected to the outlet of the drip chamber;
a first chamber disposed in the elongate body portion and including an inlet orifice fluidly coupling the first chamber to the upper surface of the elongate body portion, and an anti-run-dry membrane disposed on the upper surface of the elongate body portion extending over the inlet orifice, the inlet orifice fluidly coupled to the inlet of the drip chamber for receiving the IV fluid in a first flow condition;
a second chamber disposed in the elongate body portion and extending from the upper surface to the base portion, the second chamber having an open proximal end for receiving at least a portion of the IV fluid in a second flow condition; and
a low flowrate orifice extending from a base of the second chamber into the base portion for fluidly coupling the second chamber with the outlet of the drip chamber.

13. The drip chamber assembly of claim 12, wherein the elongate body portion further comprises a sidewall longitudinally extending between the upper surface and the base portion, and a fluid bypass orifice disposed in the sidewall, the fluid bypass orifice fluidly coupled to the outlet via the low flowrate orifice.

14. The drip chamber assembly of claim 13, wherein the inlet orifice is axially aligned with the inlet of the drip chamber.

15. The drip chamber assembly of claim 14, wherein the inlet of the drip chamber, the inlet orifice, the first chamber, the outlet orifice, and the outlet of the drip chamber are fluidly coupled to define a first fluid pathway, and in the first flow condition where the IV fluid in the drip chamber is above a predetermined level, the IV fluid flowing into the drip chamber passes through the anti-run-dry membrane and enters the first chamber via the inlet orifice.

16. The drip chamber assembly of claim 15, wherein the anti-run-dry membrane comprises a porous hydrophilic material.

17. The drip chamber assembly of claim 16, wherein the open proximal end of the second chamber, the low flowrate orifice, the outlet orifice and the outlet of the drip chamber are fluidly coupled to define a second fluid pathway.

18. The drip chamber assembly of claim 17, wherein a third fluid pathway is defined longitudinally between the sidewall of the elongate body portion and the inner surface of the housing of the drip chamber, through the fluid bypass orifice, and into the outlet orifice and the outlet of the drip chamber via the low flowrate orifice.

19. The drip chamber assembly of claim 18, wherein a fourth fluid pathway is defined (i) longitudinally between the sidewall of the elongate body portion and the inner surface of the housing of the drip chamber, (ii) circumferentially along an upper surface of the base portion between the sidewall of the elongate body portion and the inner surface of the housing of the drip chamber, (iii) through the fluid bypass orifice, and (iv) into the outlet orifice and the outlet of the drip chamber via the low flowrate orifice.

20. The drip chamber assembly of claim 19, wherein the second fluid pathway, the third fluid pathway, and the fourth fluid pathway collectively define a keep-vein-open fluid path, and in the second flow condition where the IV fluid in the drip chamber falls below the predetermined level, the anti-run-dry membrane saturated with the IV fluid restricts further fluid from flowing into the outlet via the inlet orifice such that the further fluid flows through the keep-vein-open path.

* * * * *